Figure 1:
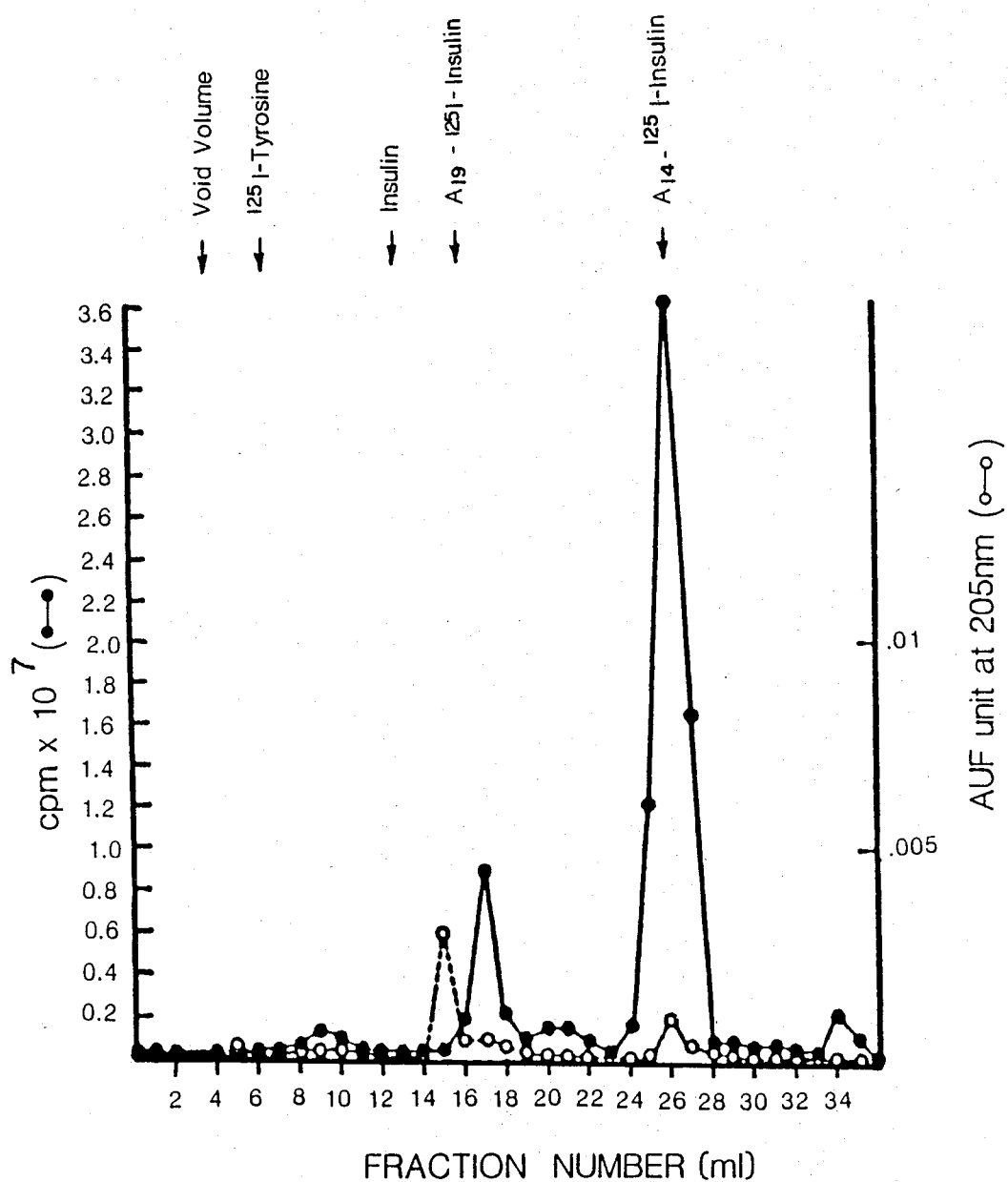

United States Patent [19]

Stentz et al.

[11] Patent Number: 4,528,134

[45] Date of Patent: Jul. 9, 1985

[54] METHOD OF SEPARATING $A_{14}$-$^{125}$I-INSULIN FROM HETEROGENEOUSLY LABELED INSULIN MOLECULES FOR BIOLOGICAL STUDIES

[75] Inventors: Frankie B. Stentz; Reba K. Wright; Abbas E. Kitabchi, all of Memphis, Tenn.

[73] Assignee: University of TN Research Corporation, Knoxville, Tenn.

[21] Appl. No.: 453,279

[22] Filed: Dec. 27, 1982

[51] Int. Cl.$^3$ .................... B01D 15/08; A61K 37/26; A61K 43/00
[52] U.S. Cl. .................... 260/112.7; 436/545; 436/804; 436/807; 424/1.1; 210/659; 210/927; 210/663; 514/3
[58] Field of Search ................. 435/71; 436/545, 804, 436/807; 424/1.1, 178; 210/659, 663, 927; 260/112.5 R

[56] References Cited

U.S. PATENT DOCUMENTS

| | | | |
|---|---|---|---|
| 3,864,325 | 2/1975 | Smyth | 260/112.7 |
| 4,337,194 | 6/1982 | Diaz et al. | 260/112.5 |
| 4,343,898 | 8/1982 | Markussen | 435/71 |
| 4,377,482 | 3/1983 | Rivier | 210/635 |

OTHER PUBLICATIONS

Stentz, F. B. et al., Diabetes, vol. 31(12), pp. 1128–1131, (12-1982).
Christensen, E. I. et al., Cell Biology International Reports, vol. 6 (8), pp. 757–765, (8-1982).
Linde, S. et al., Diabetes, vol. 30 (1), pp. 1–8, (1981).
Deng, S. et al., SSU Chuani Houeh Yuan Hsueh Pao, vol. 12 (4), pp. 275–282, (1981), (Chinese).
Jorgensen, K. H. et al., Diabetalogia, vol. 19, pp. 546–554, (1980).
Linde, S. et al., International Journal of Peptide and Protein Research, vol. 15 (5), pp. 495–502, (1980).
Danho, W. et al., Proc. Second International Insulin Symposium, pp. 59–66, (1979).
Hansen, B. et al., Proc. Second International Insulin Symposium, pp. 169–176, (9-1979).
Starr et al., *Methods of Hormone RIA*, 2nd ed., pp. 613–622, (1979).
Chard, T. *Introduction to RIA and Related Techniques*, pp. 343–375, (1978).
Hamlin, J. L. et al., J. Biol. Chem., vol. 249 (1), pp. 21–32, (1974).
Gliemann et al., Bioc. Biop. Res. Comm., vol. 87 (4), pp. 1183–1190, (1979).

*Primary Examiner*—Benjamin R. Padgett
*Assistant Examiner*—M. Moskowitz
*Attorney, Agent, or Firm*—Luedeka & Neely

[57] ABSTRACT

Method of separating $A_{14}$-$^{125}$I-insulin from heterogeneously labeled insulin molecules for biological studies which involves iodating insulin in a controlled manner, selectively absorbing the insulin from the iodination procedure in a tightly packed bed of octadecylsilane bonded to silica employing reverse phase liquid chromatography principles, thereafter eluting large and small radioactive and nonradioactive materials such as damaged insulin, various contaminants and polar materials from the bed with dilute trifluoroacetic acid, thereafter eluting the intact $^{125}$I-insulin from the bed with a mixture of acetonitrile and dilute trifluoroacetic acid and then separating the $A_{14}$-insulin by high performance liquid chromatography or ion exchange chromatography.

7 Claims, 2 Drawing Figures

METHOD OF SEPARATING $A_{14}$-$^{125}$I-INSULIN FROM HETEROGENEOUSLY LABELED INSULIN MOLECULES FOR BIOLOGICAL STUDIES

This invention was made with Government support under grants No. AM07088 and No. RR00211 awarded by the National Institute of Health. The Government has certain rights in this invention.

This invention relates generally to a method for separating $A_{14}$-$^{125}$I-insulin from heterogeneously labeled insulin molecules for biological studies and, relates more particularly to such a method which is both rapid and efficient.

The use of homogeneously labeled insulin with a high specific activity is desirable as recent work with a heterogeneous mixture of insulins has suggested that the iodinated insulin species exhibit different binding properties depending on the tissues selected. Therefore, the use of a homogeneously labeled insulin which is biologically comparable to native insulin is essential for an accurate estimation of binding kinetics.

Labeled insulin is employed in various biological studies. It has been shown that of the four tyrosine molecules in insulin, $A_{14}$ is the most similar to native insulin in regard to biological activity and properties. In the routine iodination of insulin, random labeling of the four tyrosine molecules occurs, resulting in multiple $^{125}$I-insulins with distributions of iodine atoms dependent on the average iodine atoms incorporated per insulin molecule. Although attempts have been made to purify this material by numerous methods to obtain insulin $A_{14}$ the procedures have not been entirely satisfactory because they are extremely time consuming and it is difficult to obtain reproducible results.

It is the object of this invention to provide a method for separating labeled $A_{14}$ insulin from heterogeneous insulin in a more rapid and more efficient manner.

We have discovered that insulin which has been iodinated in a controlled manner can be concentrated in such a manner that $A_{14}$-insulin can be separated from the concentrate by either high performance liquid chromatographic procedures or ion exchange chromatography in a short time with high yields.

The concentration is effected by selectively absorbing the insulin from the iodination procedure in a tightly packed bed of octadecylsilane bonded to silica employing reverse phase liquid chromatography principles. It has been found that such a bed absorbs more than 90% of the labeled insulin and that the large and small radioactive and nonradioactive materials such as damaged insulin, various contaminants and polar materials can be eluted from the bed by means of a solvent comprising dilute 0.1% trifluoroacetic acid (TFA) which may contain a small amount of acetonitrile (ACN) (ratio ACN:TFA 1 or less: 9 v/v and preferably about 1:9 v/v) during part of the elution. Thereafter, the intact $^{125}$I-insulin can be eluted with a mixture of acetonitrile and 0.1% trifluoroacetic acid having a ratio by volume of one or more parts ACN to one part TFA (preferably a ratio ACN:TFA of about 1:1 v/v).

The $A_{14}$-insulin can then be readily separated from the concentrate by either high performance liquid chromatography or by ion exchange chromatography to produce good yields of high activity $A_{14}$-insulin.

Preferably, to obtain best results, the iodination is accomplished with chloramine T (sodium para-toluene sulfachloramine) without the use of sodium metabisulfite. Iodination procedures which employ sodium metabisufite have resulted in variable yields and variability of the amount of labeled $A_{14}$-insulin.

EXAMPLE

Highly purified porcine insulin was employed. It was stored in 0.01N HCL (1 mg/ml). In order to minimize deterioration of the insulin molecules and to enhance the yield of tyrosine $A_{14}$-$^{125}$I-monoiodoinsulin, the insulin used is preferably relatively fresh, in storage less than six months and preferably less than one month.

Iodination

The insulin was iodinated to 90–100 $\mu$Ci/$\mu$g (i.e., 0.25–0.32 mole iodine/mole insulin) with chloramine T (sodium para-toluenesulfochloramine) at room temperature by the modified method of De Meyts (De Meytes, P.: Insulin and growth hormone receptors in human cultured lymphocytes and peripheral blood monocytes. In Methods in Receptor Research, Part I. Blecher, M., Ed. New York, Marcel Dekker, 1976, pp. 301–76).

Reagents were added in the following order: 40 $\mu$l of 0.3M sodium phosphate, pH 7.5; 10 $\mu$g of the purified porcine insulin in 10 $\mu$l of 0.01N HCl; 2 mCi of Na$^{125}$I in 16 $\mu$l of 0.01N NaOH, carrier-free; 0.6–1 $\mu$g chloramine T (40 $\mu$g/ml dissolved immediately before use in 0.3M sodium phosphate, pH 7.5) added stepwise in 5 $\mu$l aliquots over two minutes with agitation using a 50 $\mu$l Hamilton syringe through the septum. A sufficient amount of chloramine T was added to incorporate 45–55% $^{125}$I into trichloroacetic acid precipitable insulin. The Na$^{125}$I was from a batch having a specific activity of 14–17 mCi/mg iodine and was used within three days of availability. The chloramine T was stored in absence of light and weighed out the day of iodination.

The final concentrations of reactants were: insulin $2.0 \times 10^{-5}$M, Na$^{125}$I $1.2 \times 10^{-5}$M, chloramine T $4.0 \times 10^{-5}$M. At the end of iodination, 0.1 ml of 2.5% bovine serum albumin, which had previously been dialyzed overnight against Krebs Ringer bicarbonate, pH 7.4, was added to the reaction mixture to inhibit absorption of labeled insulin onto the glassware during transfer.

Initial Separation

An initial separation was then made in a reverse phase partition cell containing a packed bed of octadecylsilane bonded to silica employing the principles of liquid chromotography. Cells of this type are sold by Waters Associates, Milford, Mass. under the designation Sep-Pak $C_{18}$. The cartridge construction is set forth in U.S. Pat. No. 4,211,658. In brief, it includes a tri-axially packed bed with an inlet and outlet so as to provide a flow path through the bed.

Two Sep-pak $C_{18}$ cartridges were prepared by first washing the packing of each of them with 5 ml of acetonitrile (distilled in glass) followed by washing with 10 ml of 0.1% trifluoroacetic acid (sequanal grade). This was accomplished by pumping the washing material through the cartridge with a syringe. Thereafter, one-half of the iodinated mixture was pumped through the packing of each cartridge. Both wanted and unwanted materials were retained by the packing.

After the samples were loaded, each cartridge was washed by pumping 2.0 ml of a solution of 0.1% trifluoroacetic acid and acetonitrile (ratio ACN:TFA:1:9 v/v) through the bed to remove unwanted materials, e.g. the bovine serum albumin, unreacted Na$^{125}$I, and any damaged insulin.

The intact $^{125}$I-insulin was eluted from each of the Sep-Pak cartridges with three 1 ml aliquots of a solvent consisting of acetonitrile and trifluoroacetic acid (1 part by volume ACN to 1 part by volume 0.1% TFA). The majority of labeled, intact insulin was eluted in the first milliliter, which had the highest trichloroacetic acid precipitability.

Final Separation

The insulin recovered from the Sep-Pak cartridge was then treated to complete the isolation of $A_{14}$-$^{125}$I-insulin. This was accomplished by either high performance liquid chromatography (HPLC) or by ion exchange chromatography.

HPLC Procedure

Two μBondapak $C_{18}$ (10 micron) reverse phase liquid chromatography columns (Waters Associates, Milford, Mass.) were used in conjunction with Waters HPLC equipment. These columns again include a packed bed of octadecylsilane bonded to silica.

The lyophilized material from one Sep-Pak cartridge was resuspended in 100 μl of a mixture of acetonitrile and trifluoroacetic acid (34 parts by volume of ACN to 66 parts by volume of 0.1% TFA) and injected into the Bondapak columns in tandem and eluted isocratically with the above solvent system run for 40 minutes and 1 ml fractions were collected. The peak of radioactivity was assessed by counting in a gamma spectrometer and concomitant monitoring of elute absorption at 205 and 254 nm. The identification of the fractions is shown in FIG. 1.

Authenticated monoiodinated $A_{14}$-$^{125}$I-insulin (S.A. 225U Ci/mg) from Novo Research Institute, Copenhagen, Denmark, and porcine insulin were used as standards. Identification of the homogeneity of $A_{14}$-$^{125}$I-insulin was confirmed by rechromatography in the same solvent system and by sequencing of the radioactive peak material eluting with the same retention time as $A_{14}$-$^{125}$-insulin (Novo) standard on a Beckman Sequencer, Model 890C, using the SLOW PEPTIDE-DMAA (071472) program of Beckman Instruments.

Ion Exchange Chromatography Procedure

Figure 2:
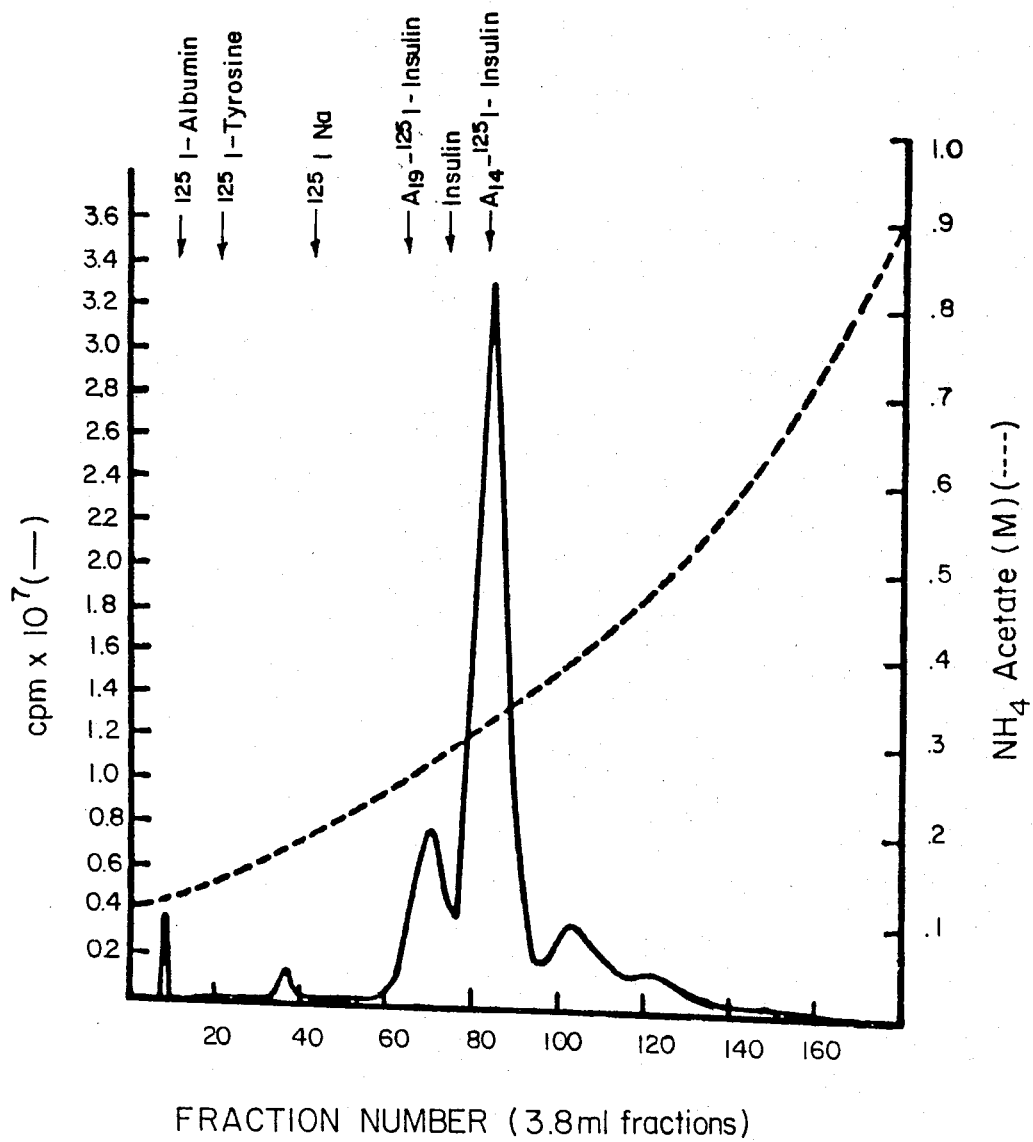

DEAE cellulose (Whatman D52) was obtained in a pre-swollen microgranular condition and suspended in 0.5M ammonium acetate, pH 9; the column (0.9×39 cm) was packed and washed with the suspension buffer. The column was then equilibrated with 0.05M sodium acetate, pH 9. 100-200 μCi of iodinated insulin free of Na$^{125}$I from the Sep-Pak cartridge was placed on top of the prepared DEAE cellulose column. The material was then eluted with a slightly concave gradient of 0.1-1M ammonium acetate, pH 9, generated by placing 125 ml of 0.1, 0.2, 0.3, 0.4, 0.5, and 1.0M buffer in each of the six chambers of a Buchler multichambered gradient maker, at a rate of approximately 0.3 ml/min for 15-20 hours at room temperature. The identification of the fractions is shown by FIG. 2. The peak fractions (3.8 ml each) of the radioactivity were pooled. Bovine serum albumin was added, and the mixture was then lyophilized and stored at −20° C. Further documentation of $A_{14}$-$^{125}$I-insulin was accomplished by rechromatography on HPLC and/or sequencing of the labeled insulin.

Rechromatography on HPLC of $A_{14}$-$^{125}$I-insulin peaks purified by both methods produced a single peak with a retention time of 26 minutes and no detectable absorbance at 15 minutes, the retention time of unlabeled insulin, indicating a specific activity of 360 mCi/mg. Specific activity assessed by TCA precipitation and radioimmunoassay at each step of purification is given in Table 1 along with the yield of labeled insulin.

$^{125}$I radioactivity measured after thirty cycles of sequencing of the $A_{14}$-$^{125}$I-insulin peak on a Beckman Sequencer was found only in the products of cycle 14, confirming the position of $^{125}$I at tyrosine 14.

TABLE 1

Profile of Specific Activity of Labeled Insulin During Different Stages of Purification

| Step | Yield (uCi) | Specific Activity (mCi/mg) | % TCA Precipitable |
|---|---|---|---|
| 1. Iodination mixture | 1000 | 100 ± 10 | 50 |
| 2. Sep Pak | 800 | 130 ± 10 | 96 |
| 3. DEAE Cellulose | 220 | 275 ± 25 | 99 |
| 4. HPLC | 200 | 360 | 99 |

From the foregoing, it will be seen that the initial separation which involves the use of a packed bed of silica and octadecane together with the proper choice of solvents to effect the selective elution of the unwanted materials followed by the elution of the remaining materials to produce labeled insulins with only a minimum amount of unwanted materials makes possible the subsequent separation and isolation of $A_{14}$-insulin in a rapid and expeditious manner.

Various of the features of the invention which are believed to be novel are set forth in the appended claims.

We claim:

1. Method of preparing $A_{14}$-$^{125}$I-insulin comprising the steps of iodinating insulin with $^{125}$I to produce an iodinated mixture containing heterogenous labelled insulin and unwanted materials, and separating the $A_{14}$-$^{125}$I-insulin in a separation having a first stage and a second stage, said first stage comprising absorbing said iodinated mixture in a packed bed of octadecylsilane bonded to silica, eluting said unwanted materials from said bed with a 0.1% solution of trifluoroacetic acid while retaining said labelled insulin, and eluting said labelled insulin from said bed with a solution of 1 or more parts by volume of acetonitrile to 1 part by volume of 0.1% trifluoroacetic acid to produce a labelled insulin concentrate, said second stage comprising separating the $A_{14}$-$^{125}$I-insulin from said concentrate.

2. The method of claim 1 wherein the solution for eluting the insulin from said bed comprises about 1 part by volume of acetonitrile and 1 part by volume of 0.1% trifluoroacetic acid.

3. The method of claim 1 wherein the elution of unwanted materials is effected by a first elution with 0.1% trifluoroacetic acid and a second elution with a solvent comprising 0.1% trifluoroacetic acid which contains a small amount of acetonitrile.

4. The method of claim 3 wherein the elution of unwanted materials is effected by a first elution with 0.1% trifluoroacetic acid and a second elution with a solvent comprising 1 part by volume of acetonitrile and 9 parts by volume of 0.1% trifluoroacetic acid.

5. The method of any of claims 1-4 wherein the iodination is effected with chloramine T.

6. The method of any of claim 1 through 5 wherein the $A_{14}$-$^{125}$I-insulin is separated from said concentrate in said second stage by high performance liquid chromatography in a packed column containing a bed of octadecylsilane bonded to silica with a solvent comprising acetonitrile and 0.1% trifluoroacetic acid in a volume ratio of about 1 to 2.

7. The method of any of claims 1 through 5 wherein the $A_{14}$-$^{125}$I-insulin is separated from the insulin contained in said concentrate in said second stage by ion exchange chromatography in a column of microgranular cellulose with a solvent system of 0.1–1M ammonium acetate, pH 9, with a sequential graduation from 0.1 to 1M.

* * * * *